United States Patent [19]
Krivoshlykov

[11] Patent Number: 5,903,696
[45] Date of Patent: May 11, 1999

[54] MULTIMODE OPTICAL WAVEGUIDES, WAVEGUIDE COMPONENTS AND SENSORS

[75] Inventor: Sergej G. Krivoshlykov, Moscow, Russian Federation

[73] Assignee: CeramOptec Industries Inc, East Longmeadow, Mass.

[21] Appl. No.: 08/865,555

[22] Filed: May 29, 1997

Related U.S. Application Data

[63] Continuation of application No. 08/426,098, Apr. 21, 1995, abandoned.

[51] Int. Cl.$^6$ ............................................. G02B 6/22
[52] U.S. Cl. ........................ 385/127; 385/144; 385/145; 385/129; 385/132
[58] Field of Search .................................. 385/123–128, 385/129, 141–145, 132

[56] References Cited

U.S. PATENT DOCUMENTS

| | | | |
|---|---|---|---|
| 4,770,492 | 9/1988 | Levin et al. | 350/96.29 |
| 4,830,463 | 5/1989 | Lemaire et al. | 385/123 |
| 4,877,304 | 10/1989 | Bhagavatula | 385/123 |
| 4,889,404 | 12/1989 | Bhagavatula et al. | 385/123 |
| 5,056,888 | 10/1991 | Messerly et al. | 385/123 |
| 5,170,457 | 12/1992 | Jen | 385/123 |

OTHER PUBLICATIONS

J. Hecht, "Understanding Fiber Optics" cover, ii, p. 57 (1987) Howard W. Sams & Co (publisher–Indianapolis, IN).

*Primary Examiner*—John Ngo
*Attorney, Agent, or Firm*—Bolesh J. Skutnik; BJ Associates

[57] ABSTRACT

The invention describes two types of multimode optical waveguides having special dip in the refractive index profile of their core providing conditions for propagation of a higher order mode with sharp central peak which field carries considerable part of the mode energy, while the fields of all other modes in the waveguide are mostly concentrated outside of this central peak region. The waveguide of the first type guides the mode only with one central peak while the mode in the waveguide of the second type has also an additional peak at the interface between the waveguide core and cladding providing a possibility to detect any influence on the mode field in its outer region by measuring the signal in the central peak of the mode.

The useful properties of these two kinds of modes can be employed for designing new wavelength selective waveguide components for optical communications and sensors applications: an optical waveguide modulator, amplitude and interferometric sensors for different applications, bistable nonlinear components for logic switching and optical memory, wavelength selective chemical sensors of both amplitude and interferometric type, etc. Employing a material exhibiting electro-optical properties provides a possibility of tuning of the components proposed as well as fabrication of the sensors of electric fields.

36 Claims, 11 Drawing Sheets

1. Nonlinear multimode waveguide
2. Single-mode input/output waveguides
3. Optical feedback

MULTIMODE OPTICAL WAVEGUIDES, WAVEGUIDE COMPONENTS AND SENSORS

This application a continuation of U.S. patent application Ser. No. 08/426,098 filed on Apr. 16, 1995 now abandoned by Sergej G. Krivoshlykov, inventor, entitled "MULTIMODE OPTICAL WAVEGUIDES, WAVEGUIDE COMPONENTS AND SENSORS", and incorporated by reference herein.

BACKGROUND OF THE INVENTION

1. Field of the Invention

The invention relates generally to optical waveguides, optical waveguide components for signal processing and optical waveguide sensors for various physical fields, and more specifically to multimode optical waveguides having a specific refractive index profile of their core providing a possibility to guide a higher order mode with sharp central peak of its field and to optical components and sensors based on this waveguide designed for optical fiber communication systems, sensor systems and other optical devices for industrial and medical applications.

2. Information Disclosure Statement

Integrated optical waveguides and optical fibers are key components of optical fiber communication systems, optical sensors and other optical devices for various industrial and medical applications. All these components and sensors essentially consist of an optical waveguide having a core region and outer cladding with lower refractive index. Many types of various optical waveguide components and sensors have been developed for different industrial and medical applications.

The most sensitive sensors and the most commonly used waveguide components for optical fiber communication systems usually employ single-mode waveguides or fibers since these waveguides provide good compatibility with typical single-mode fiber network and reduced modal noise. Employing the single-mode waveguide in optical sensors provides a possibility to design interferometric sensors which are much more sensitive than the sensors of amplitude type. The multimode waveguides having larger cross section than single-mode waveguides, however, are basically more convenient to deal with in practice. In some specific applications such as chemical sensors based of Fourier spectroscopy in middle infrared range of spectrum, moreover, one must use multimode fibers since single-mode fibers operating in middle infrared are not available. The modal noise of speckle pattern resulting form the interference of many modal fields in a multimode waveguide is the main problem to be overcome in order to employ these waveguides especially in interferometric sensors and components. Therefore, multimode waveguides are usually used only in sensors of amplitude type where the sum of intensities of all waveguide modes is detected. Sensitivity of such sensors, however, is much lower than the sensitivity of single-mode interferometric sensors. Therefore it is very important to design highly sensitive sensors and components based on multimode rather than on single-mode waveguides. This problem can be solved by providing a single-mode regime of operation in the multimode waveguide since each selected mode is more sensitive to external influence to be detected than whole set of the modes carried by the waveguide.

It have been proposed to use computer generated holograms for selective excitation and detection of some specific modes inside a multimode fiber in order to realize sensors with enhanced and tunable sensitivity by switching from one operating mode to another. This method being very attractive from physical point of view is practically not very convenient since it is difficult to integrate the computer generated holograms in a standard single-mode optical fiber network. It is desirable to have a possibility of creating a single mode regime of operation in a multimode waveguide without employing the computer generated holograms, which usually also require complicated input-output optics.

OBJECTS AND SUMMARY OF THE INVENTION

It is an object of the present invention to describe a new type of multimode optical waveguide which can guide a higher order mode of special shape having sharp peak of its field in the waveguide center region, which carries the main part of the mode energy, and which can be easily selected from other modes with the help of an appropriate aperture.

Another object of the invention is to specify a construction of wavelength selective components for optical signal processing based on such waveguide which can be both an integrated optical waveguide and an optical fiber.

It is a further object of the invention to describe amplitude and interferometric optical waveguide sensors for various applications with enhanced sensitivity employing the proposed multimode waveguides.

Another object of the invention is to propose such multimode waveguide having a higher order mode with two peaks. One peak is located in the waveguide center. A second peak is located at the interface between the waveguide core and thin additional cladding. This structure provides a possibility to detect variations of the field in the cladding region by detecting a signal in the central region of the waveguide.

Still other object of the invention is to specify a wavelength selective chemical sensor with enhanced sensitivity based on multimode integrated optical waveguides or multimode optical fibers.

Other object of the invention is to provide a method of effective light coupling between a mode of the multimode waveguide under operation and a single-mode optical fiber network.

Briefly stated, the present invention describes two types of multimode optical waveguides having a special dip in the refractive index profile at their core's center which provids conditions for propagation of a higher order mode with sharp central peak of its field carrying considerable part of the mode energy. The fields of all other modes in the waveguide are mostly concentrated outside of this central peak region. The waveguide of the first type guides a mode with only one central peak while the mode in the waveguide of the second type has also an additional peak at the interface between the waveguide core and cladding providing a possibility to detect any influence on the mode field in its outer region by measuring the signal in the central peak of the mode.

The useful properties of these two kinds of modes can be employed for designing new wavelength selective waveguide components for optical communications and sensors applications: an optical waveguide modulator, amplitude and interferometric sensors for different applications, bistable nonlinear components for logical switching and optical memory, wavelength selective chemical sensors of both amplitude and interferometric type, etc. Furthermore, employing a material exhibiting electro-optical properties provides a possibility of tuning of the components proposed as well as realization of the sensors of electric fields.

The above, and other objects, features and advantages of the present invitation will become apparent from the following description read in conjunction with the accompanying drawings, in which like reference numbers in different drawings denote like items.

BRIEF DESCRIPTION OF DRAWINGS

FIG. 2 (b) shows a field profile for typical higher order mode without the sharp peak in its central region.

FIG. 10 (b) shows a typical configuration of the mode field having one sharp central peak and two sharp side peaks.

DESCRIPTION OF PREFERRED EMBODIMENTS

In order to achieve the goal of this invention, propagation in a multimode optical waveguide of a higher order mode with a sharp central peak, we have investigated field configurations for the transverse modes in a multimode waveguide having various shapes of its core refractive index profile. It has been found that waveguides of different kinds, such as planar waveguides, rib waveguides and optical fibers with a circular cross section, having refractive index profile with a dip minimum in its center region, under certain conditions can guide a specific type of higher order mode whose field while filling the whole cross section of the waveguide has a sharp peak in the waveguide's central region. The central mode field peak carries a considerable part of the mode energy and its width can be controlled and matched to the width of the fundamental mode of a standard output single-mode fiber network, if required.

Figure 1A:
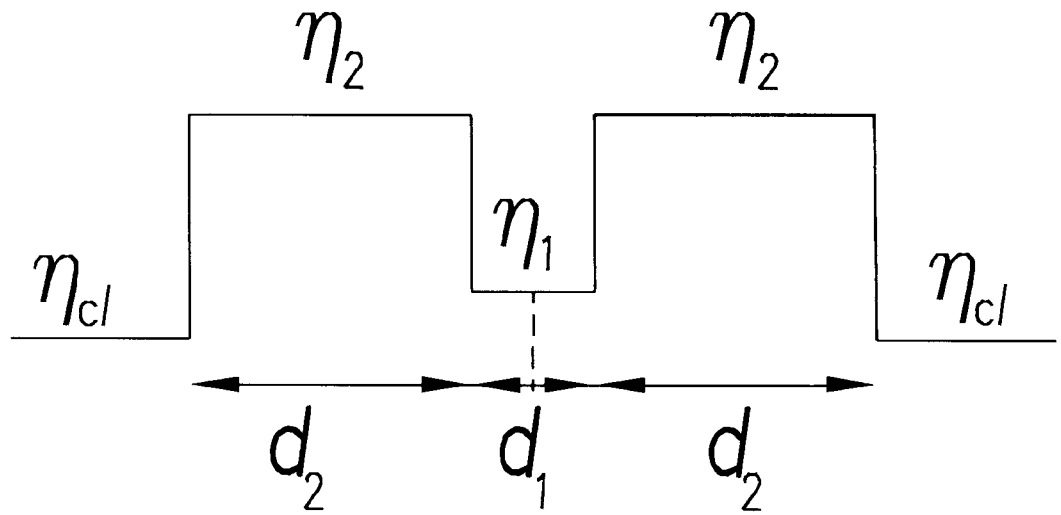
FIG. 1(a) shows a schematic view of the refractive index profile for the multimode optical waveguide having a central dip in its core region.
Figure 1B:
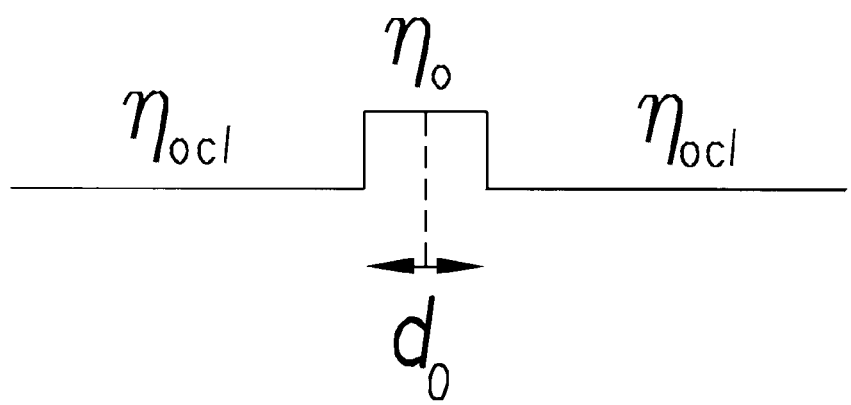
FIG. 1 (b) shows a schematic view of the refractive index profile for typical single-mode optical waveguide.

An example of the multimode planar waveguide with such a compound refractive index profile is schematically shown in FIG. 1 (a). In this preferred embodiment it is constructed in the following way. The width $d_1$ and refractive index $n_1$ of the dip in the central region of the fiber core have been chosen to be equal to the width $d_0$ and refractive index $n_0$ of typical single-mode waveguide as well as the refractive index of the cladding $n_{cl}=n_{0cl}$, as shown in FIG. 1 (b). There are quite a number technologies available that can be used to fabricate the waveguide with such a refractive index profile. For example, in the case of optical fiber waveguide one can draw such a fiber from a preform fabricated using the method of plasma chemical vapor deposition. A refractive index profile of typical single-mode fiber is shown in FIG. 1 (b) for comparison. Outer region of the core of the multimode fiber in FIG. 1 (a) has much higher refractive index $n_2>n_1>n_{cl}$ and much larger size $d_2>d_1$ than its central region providing a multimode regime of operation over the whole core of the compound waveguide. Optimization of the compound refractive index profile in order to obtain the desired field configuration in the resulting waveguide can be performed numerically using standard software for evaluation on the mode fields in corresponding slab, rib or fiber waveguides which is available commercially.

Figure 2A:
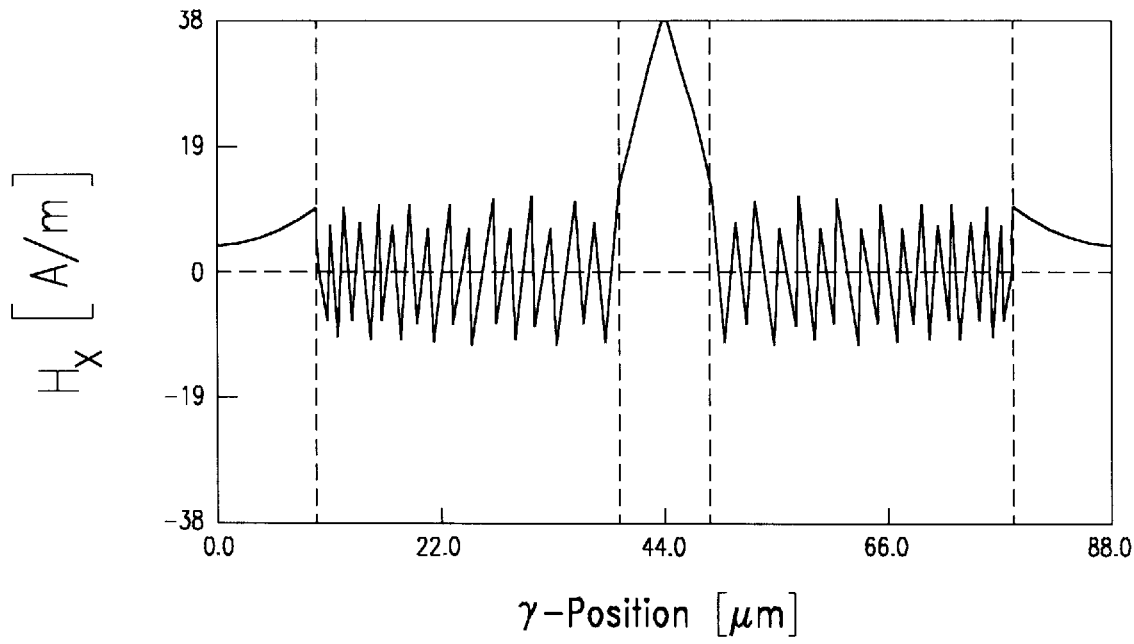
FIG. 2 (a) shows a field profile for the higher order mode with a sharp peak having a maximum in its central region.
Figure 2B:
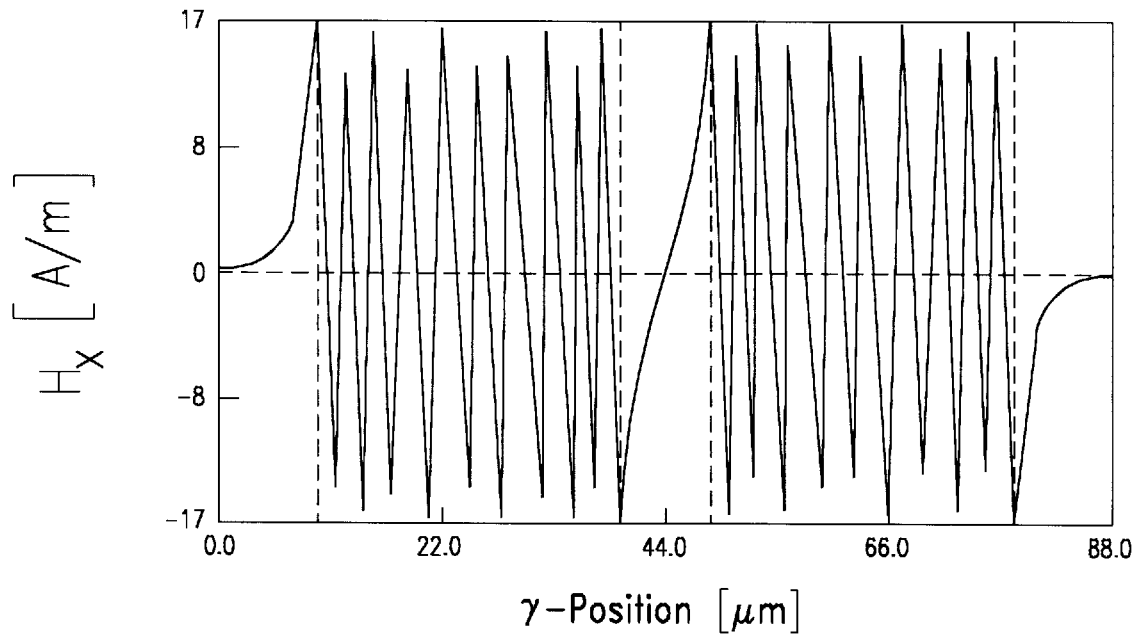
Figure 3A:
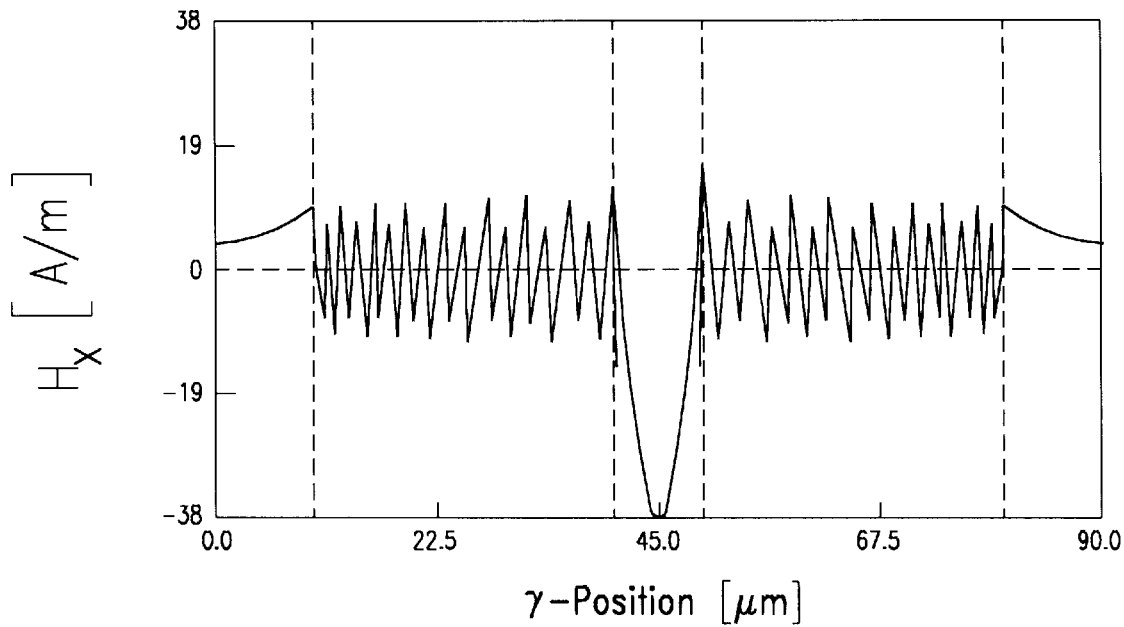
FIG. 3 show typical field profiles for the higher order mode with sharp peak having a minimum in its central region.
Figure 3B:
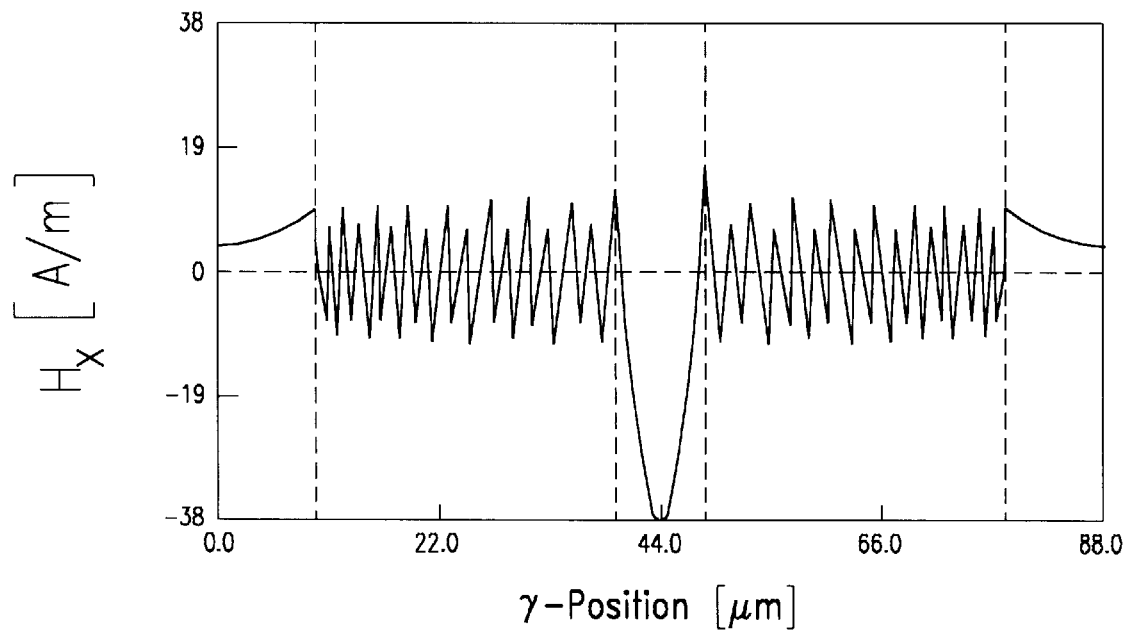

For example, the field configuration of a higher order mode in the compound slab waveguide having a sharp central peak of its field is shown in FIG. 2 (a) in the case when the wavelength of radiation $\lambda=1.55$ $\mu$m, $n_{cl}=n_{0cl}=1.460$, $n_1=n_0=1.463$, $d_1=d_0=8$ $\mu$m and $d_2=30$ $\mu$m, $n_2=1.65$. A physical reason for origin of such a higher order mode having sharp peak of its field in the central region of the waveguide can be explained as follows. It is known that the intensity of mode field increases at the interface between the waveguide and a medium with lower refractive index. Therefore, two symmetric higher order modes corresponding to the right and to the left parts of compound waveguide profile shown in FIG. 1 (a) and having refractive indices $n_2$ have sharp peaks (either maximum or minimum) of their fields just in the central region of the waveguide. An appropriate choice of the waveguide thickness $d_2$ and refractive index $n_2$ results in a constructive interference of these two modes resulting in the desired higher order mode of whole compound waveguide with sharp peak in the waveguide center as shown in FIG. 2 (a). FIG. 3 shows two typical mode field configurations having sharp peak with minimum of their fields in the central region for different combination of the waveguide parameters. FIG. 3 (a) corresponds to the case $\lambda=1.55$ $\mu$m, $n_{cl}=1.460$, $n_1=1.463$, $d_1=8$ $\mu$m, $n_2=1.65$ and $d_2=31$ $\mu$m, while FIG. 3 (b) corresponds to the case $\lambda=1.55$ $\mu$m, $n_{cl}=1.460$, $n_1=1.463$, $d_1=8$ $\mu$m, $d_2=30$ and $n_2=1.686$. In all the cases shown either in FIG. 2 (a) or FIG. 3 the width of central peak of the field can be adjusted by changing the refractive index $n_1$ and thickness $d_1$ of the central region of the waveguide.

A typical field configuration of other higher order mode which does not have a peak of the field in the central region of the waveguide is shown in FIG. 2 (b). The field of these modes are mostly concentrated in the outer regions of the waveguide core having higher refractive index $n_2$. Using an appropriate aperture in the central region of the waveguide it is possible to select the field corresponding to the central peak of desired mode while filtering all other higher order modes.

Computer generated holograms can also be employed for selection of the field of one specific mode that is an example of more complicated technical solution of the problem. Butt-joining of the compound waveguide with some single-mode output waveguide provides another possibility for selection of the field corresponding to the central peak of the mode. A field of the fundamental mode in a single-mode waveguide with the same values of parameters $\lambda=1.55$ $\mu$m, $n_{0cl}=1.460$, $n_0=1.463$ and $d_0=8$ $\mu$m is shown in FIG. 4 for comparison.

Figure 4:
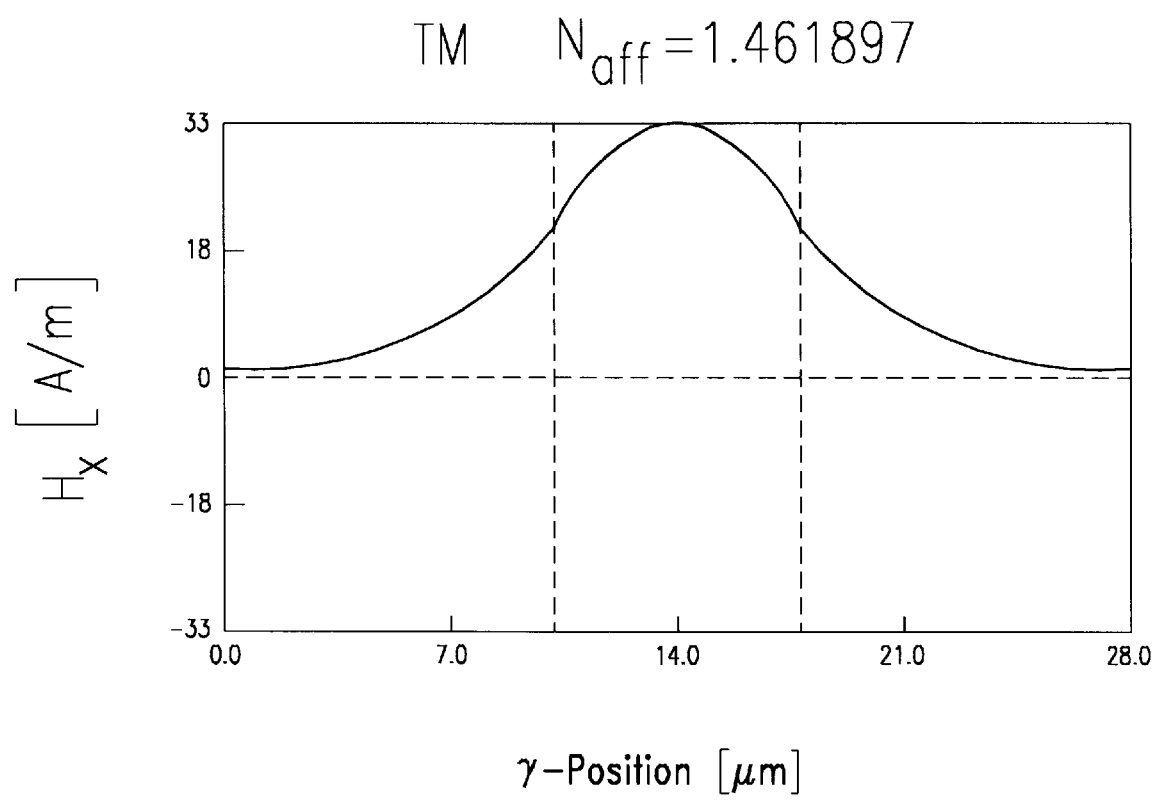
FIG. 4 shows a field of the fundamental mode in typical single-mode optical waveguide.

One can see that by appropriate adjusting the width of the compound waveguide $d_1$ it is possible to match the width of central peak of the field in FIG. 2 (*a*) to the width of the fundamental mode in FIG. 4 so as to maximize an overlap integral between these two fields thus providing a maximum coupling efficiency to a single-mode output waveguide. Moreover, the mode field configurations in the compound multimode waveguide shown in FIG. 2 (*a*) and in FIG. 3 keep their shapes while changing the width of the central peak of the mode field up to the value of the core central region as large as $d_1$=15 µm. In the case of a single-mode waveguide shown in FIG. 4 the single-mode regime of operation brakes down already at the value $d_1$>8.2 µm. Thus, the multimode waveguide of this invention is able to guide a single-mode-like higher order mode with sharp peak even when width $d_1$ of the dip of its core profile twice as large as the width of the core of the single-mode waveguide.

The profile optimization process of the mode field described in the above example in detail may be different for different types of optical waveguides (planar, rib waveguides, optical fibers) and it obviously depends on each specific application of the waveguide and each specific output mode field configuration to be obtained. However, a person skilled in the art is well capable by following the above example and the general disclosure to carry out such optimization and adaptation following established waveguide theories. Therefore, one specific example given above does not restrict all other possible applications of the mode field configuration with a sharp central peak as proposed.

Designing optical waveguide components and sensors is one of the most important applications for the described higher order mode configuration with sharp central peak. A mode field resulting from a constructive interference of two higher order modes in the right and the left parts of the compound waveguide core under certain conditions can be made very sensitive to variations of both the core refractive index $n_2$ and core thickness, $d_2$, while good quality output beam is provided by the selection of the central peak of the mode field for measurement. This selection procedure can also be used to provide a feedback just for this specific mode of the multimode waveguide, when it is required for its stabilization. The feedback can easily be realized in a standard way using either semitransparent mirrors at the end faces of the waveguide or a loop of a single-mode fiber. The feedback can conveniently be combined with the mode field selection described above by combining the computer generated holograms or aperture with mirrors or feedback fiber loop.

Figure 5:
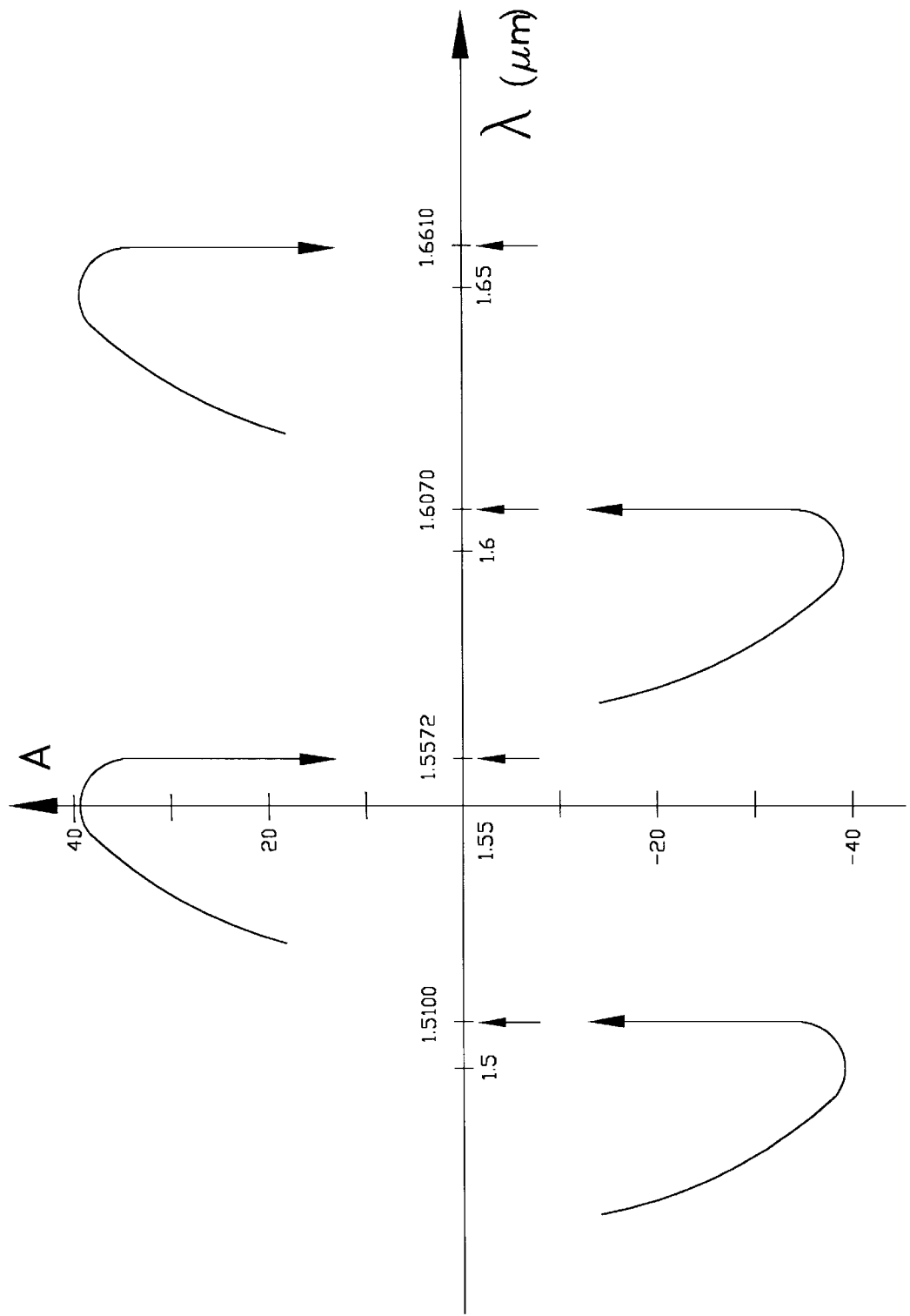
FIG. 5 shows the dependence of the normalized amplitude of the central mode peak on the wavelength.
Figure 6:
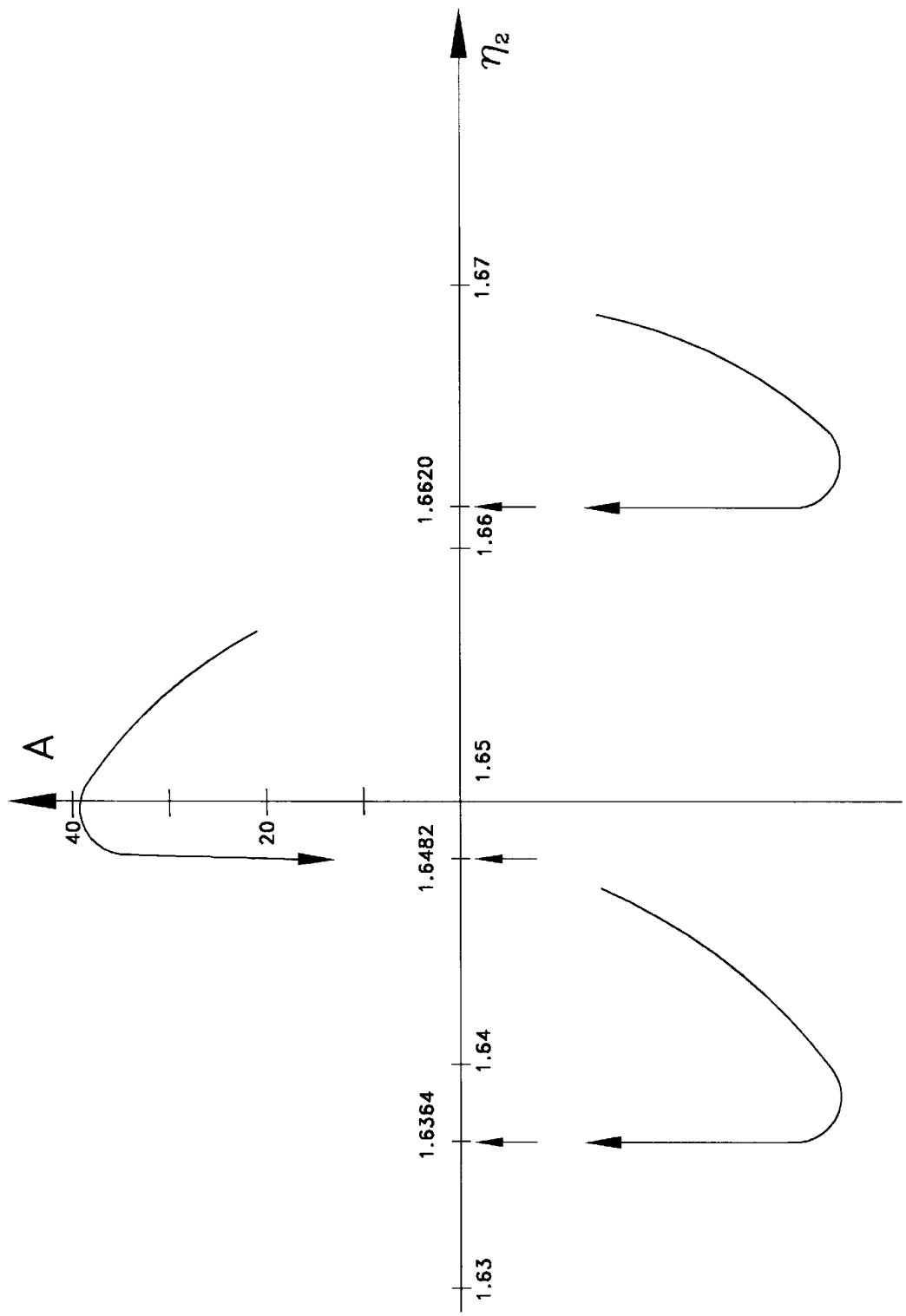
FIG. 6 shows the dependence of the normalized amplitude of the central mode peak on the core refractive index $n_2$.

The conditions under which a mode with a sharp central peak of its field appears depend on the waveguide profile parameters and the operating wavelength $\lambda$. Changing the wavelength results in a periodic construction and destruction of the mode structure with a sharp central peak each time that the whole number of guided modes in the waveguide increases by one. The normalized amplitude of the peak of the mode field in the waveguide center as a function of wavelength is illustrated in FIG. 5. The figure shows periodic dependence of the system transmission as a function of wavelength. Thus, the waveguide being tuned to an appropriate working point can operate as a narrow band filter. For example, the cutoff of the filter bands represented in FIG. 5 correspond to the wavelengths $\lambda$=1510.0 nm, 1557.2 nm, 1607.0 nm, 1661.0 nm, etc. Increasing the wavelength at these points by only 0.1 nm results in a drastic decrease of the central peak of the mode field. The wavelength selectivity of the field configuration with sharp central peak can be employed to design different wavelength selective components for optical communications and sensors applications. This is another advantage of the proposed waveguide.

The amplitude of a central peak of the mode field has similarly a periodic dependence on both waveguide core refractive index $n_2$ and waveguide thickness $d_2$. The normalized amplitude of the central peak of the waveguide mode as a function of refractive index $n_2$ is represented in FIG. 5. The dependence of the intensity of the output beam resulting from the selected central peak on the core refractive index $n_2$ can be used to design optical waveguide modulators and amplitude sensors. The amplitude of the peak of the output beam breaks down in the points of cutoff corresponding to the refractive index $n_{2cut}$=1.6364, 1.6482, 1.6620, etc. if the index is decreased by the value as small as $10^{-4}$–$10^{-5}$. Thus, electro-optic, acousto-optic, thermo-optic effects or $\chi^{(3)}$—nonlinearity of core material can be used for such an amplitude modulation if one fabricates the waveguide core from appropriate electro-optical, acousto-optical or nonlinear materials.

In one preferred embodiment of electro-optical amplitude modulator, a set point of the waveguide should just be tuned to a corresponding refractive index $n_{2cut}$, but remaining still below this value. Under such condition an electro-optical modulation of the core refractive index as small as $10^{-4}$ results in strong modulation of the light intensity of the waveguide output. In another preferred embodiment of an all-optical modulator, the modulation of the output intensity can be achieved by irradiating the core made from material having third-order nonlinearity with another modulating optical beam which causes variation of the core refractive index.

Figure 7:
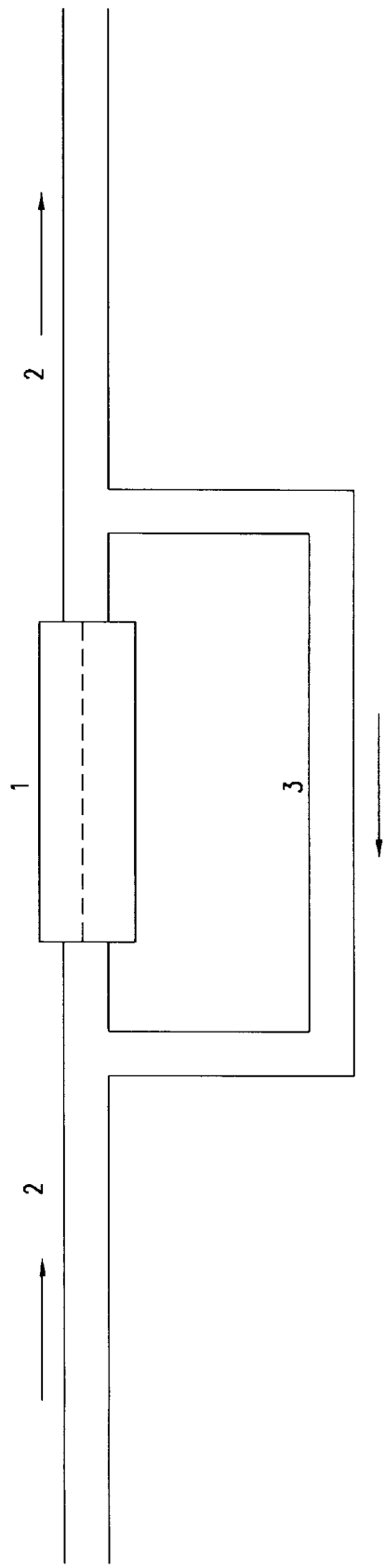
FIG. 7 shows an example of optical waveguide with third-order nonlinearity having a feedback.

Possibility of high nonlinear optical response in the waveguide system having third-order nonlinearity of the core material, as described above, can be used in a large number of all-optical devices. For instance, the nonlinear waveguides being supplied with an optical feedback can be employed in all-optical bistable waveguide components or intensity stabilizers. An example of the waveguide component with optical feedback is schematically shown in FIG. 7. In the case of optical stabilizer one should adjust the waveguide to such a set point that increasing the light intensity changes the core refractive index to increase the output beam intensity, and decreasing the light intensity changes the core refractive index so as to increase the output light intensity. Under certain conditions the optical nonlinearity of the component with optical feedback can result in bistability when the system under consideration can exist in one of two stable states for a given incident light intensity depending on its history. The bistable components can find many useful applications in different all-optical devices, for example, such as logic switching components or optical memory.

Figure 8A:
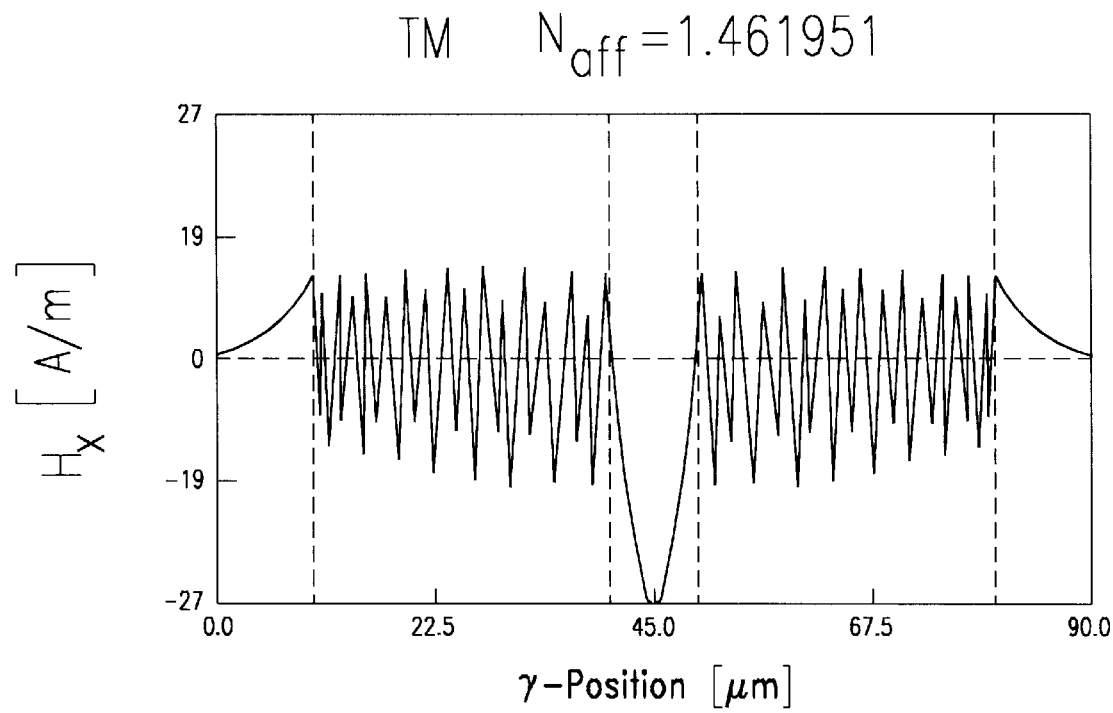
FIG. 8 shows field configurations for two modes having sharp central peaks.
Figure 8B:
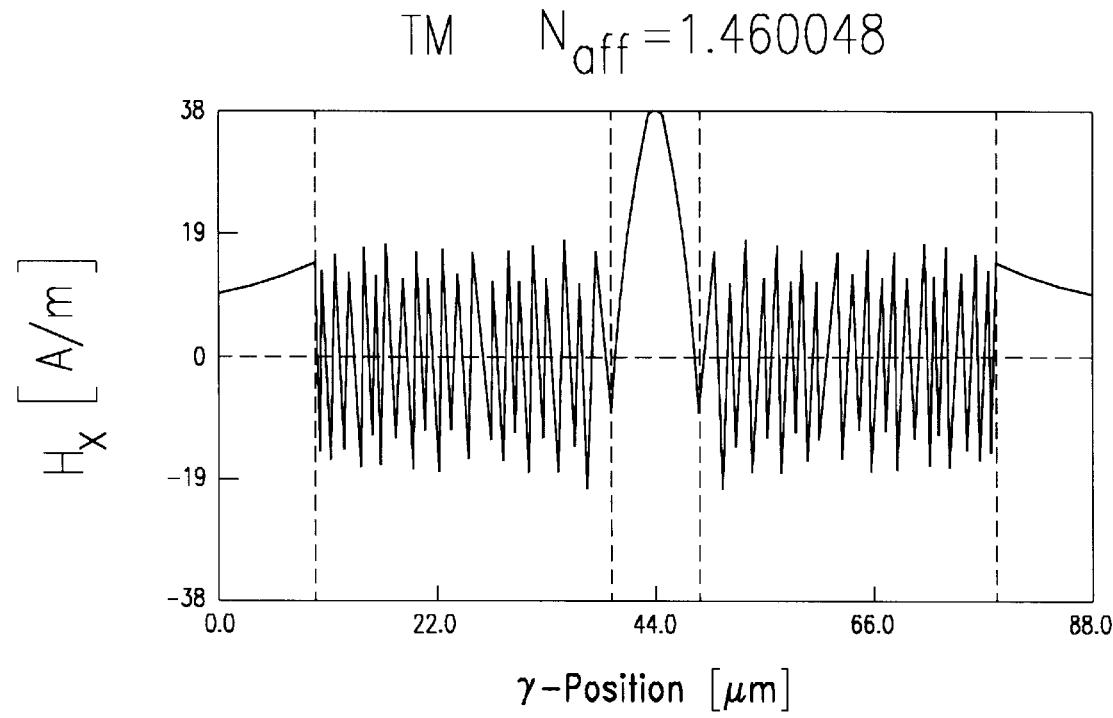

Under certain conditions one can get such regime of operation when the waveguide guides two higher order modes with sharp central peaks having almost equal intensities in their maximum. An example of field distributions for such two modes in shown in FIG. 8 in the case when $n_{cl}$=1.46, $n_1$=1.463, $n_2$=1.65, $d_1$=10 µm, $d_2$=30 µm and $\lambda$=1.482 µm. Since propagation constants for these modes are different, the phase difference between them responsible for their interference is a periodic function of the waveguide's length resulting in a periodic increasing and decreasing the sum of fields of two modes in the central region of the waveguide where the field intensity is detected. This effect provides a possibility to produce an interferometric sensor based on one multimode waveguide employing the interference between these two specific waveguide modes. An important advantage of this interferometric sensor, being compared with standard interferometers that are based on single-mode waveguides, is a possibility to delete the second waveguide used as a reference arm. This provides a possibility to enhance stability of the device, for example, with respect to temperature variations. Interferometric sensors of such a type can be used to detect any physical field resulting in a variation of the waveguide geometry or refractive index profile as a variation of the output intensity in the waveguide central region.

Figure 9A:
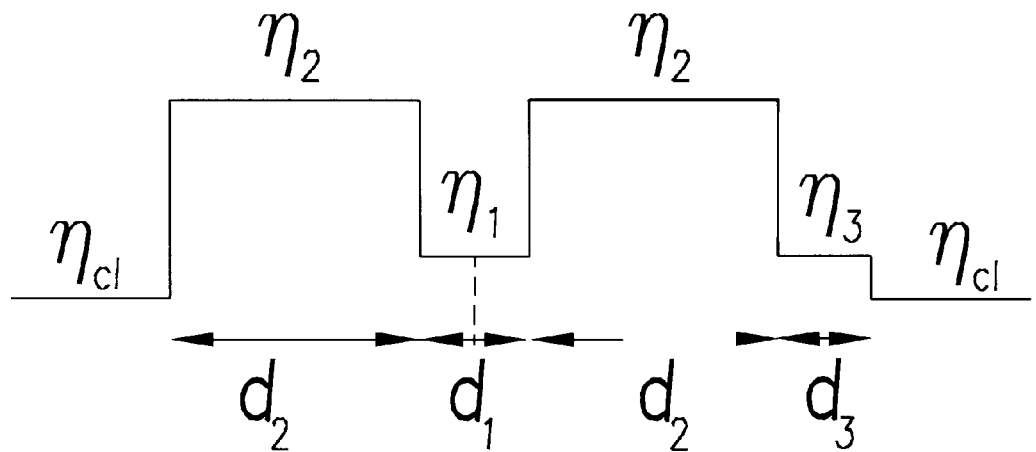
FIG. 9 shows a typical refractive index profile for the waveguide with additional cladding layer (a) on one side and (b) on both sides.
Figure 9B:
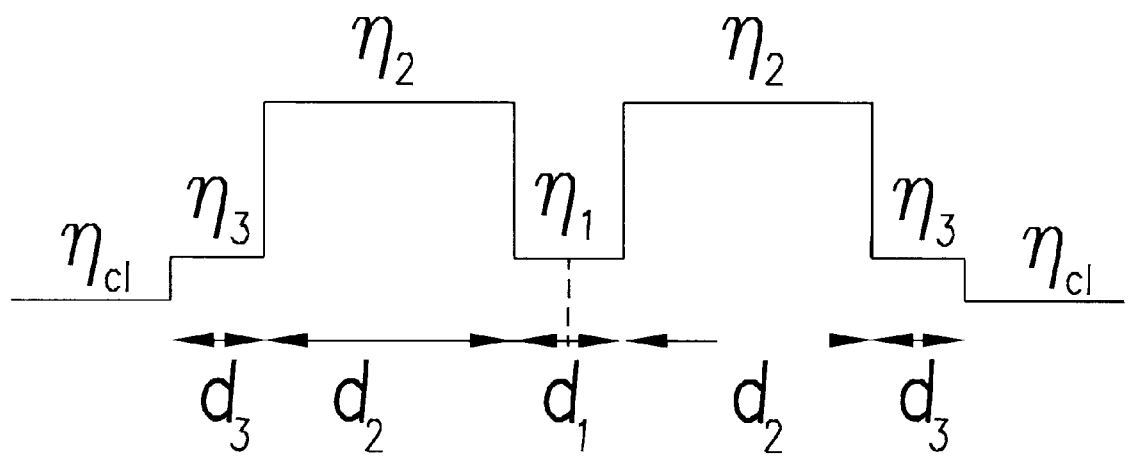
Figure 10A:
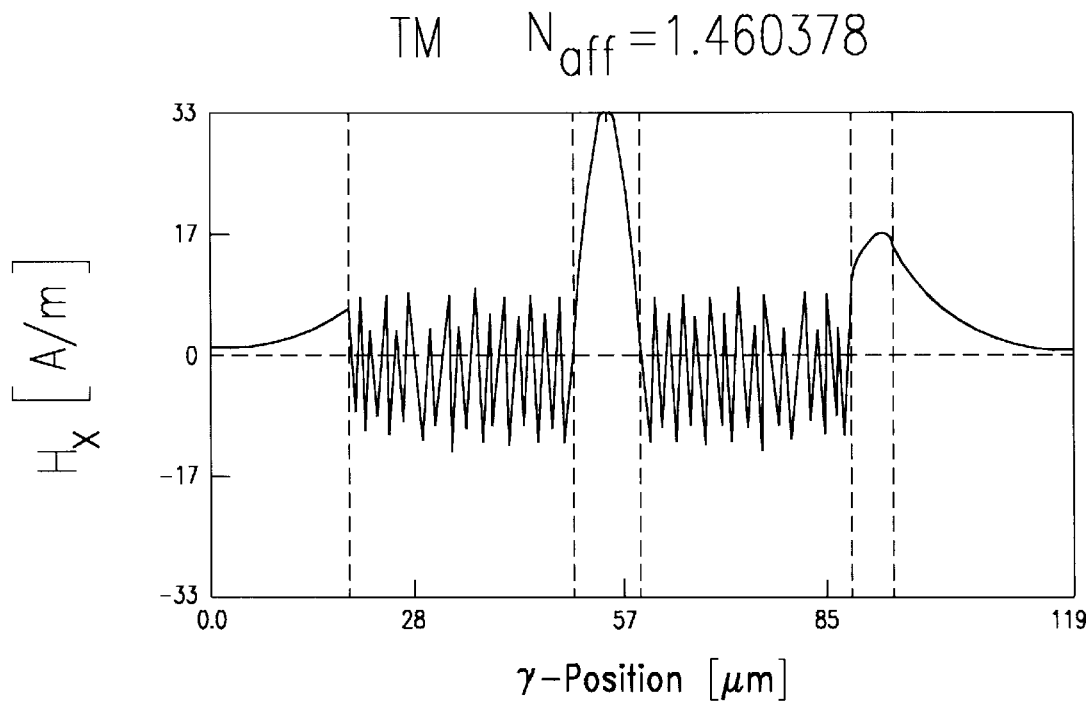
FIG. 10 (a) shows a typical configuration of the mode field having one sharp central peak and one sharp side peak.
Figure 10B:
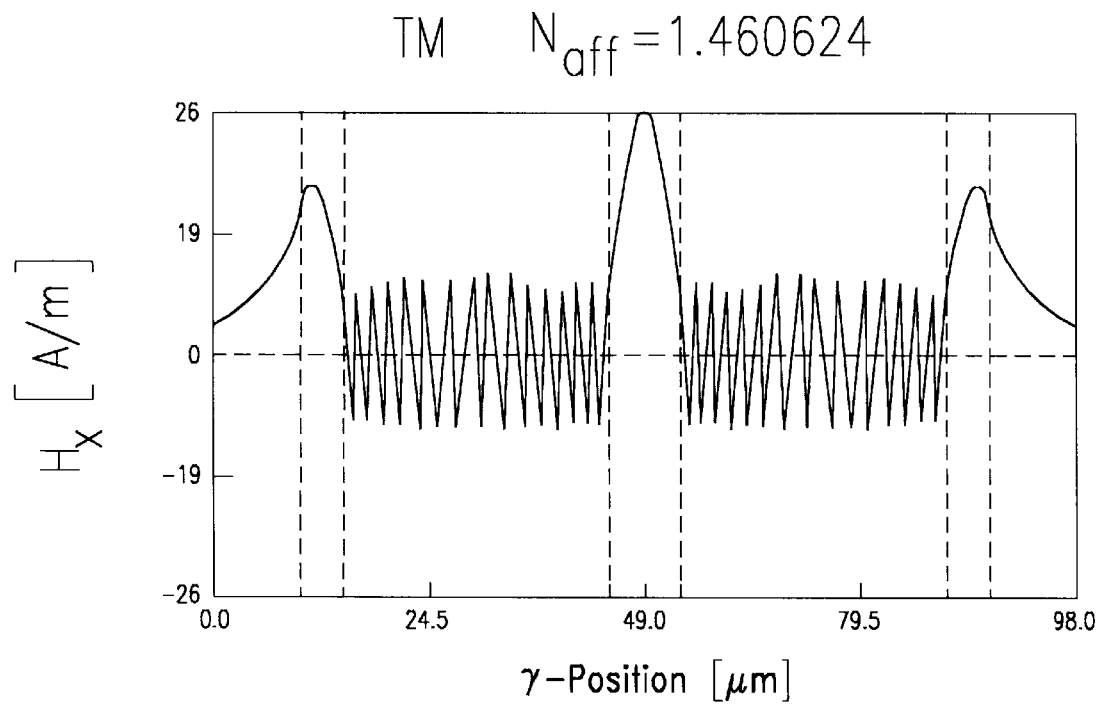

The described properties of a higher order waveguide mode with sharp central peak can also be used to design another type of waveguide useful for chemical sensor applications. Adding to the waveguide core an outer lower refractive index optical layer at least from one side of the core results in a higher order mode having both a sharp central peak and a sharp side peak in its field distribution. FIG. 9 shows a refractive index profile in the waveguide with one (a) or two (b) such additional cladding layers having refractive index $n_3$ and thickness $d_3$. FIG. 10 (a) shows a mode field with one additional side peak in the case of the waveguide having one additional cladding layer, while FIG. 10 (b) illustrates the similar mode with two side peaks in the case of a symmetrical waveguide having two outer lower index layers. Both modes shown in FIG. 10 correspond to the case when $n_{cl}=1.46$, $n_1=1.463$, $n_2=1.65$, $n_3=1.463$, $d_1=8$ $\mu$m, $d_2=30$ $\mu$m, $d_3=5$ $\mu$m and $\lambda=1.55$ $\mu$m. Such mode configurations in a multimode waveguide can be employed to design different chemical sensors based either on the methods of Fourier spectroscopy or on simple detection of optical signal as a function of the concentration of substance to be detected. Moreover, for some specific applications it is very important to be able to employ just multimode waveguides in chemical sensors. It is known that the meddle infrared region of spectrum corresponds to fingerprints of many practically important substances to be detected using the methods of diode laser or Fourier transform spectroscopy. Almost all fibers designed to operate in the middle infrared range of spectrum have multimode core with large cross section. Therefore it is important to have a possibility to operate just with the multimode fibers in the chemical sensors. The next important advantage of the chemical sensors based on multimode waveguides of such type is a possibility of designing wavelength selective sensors adjusted to some specific wavelength corresponding to the peak in the absorption spectrum of the substance to be detected.

Figure 11A:
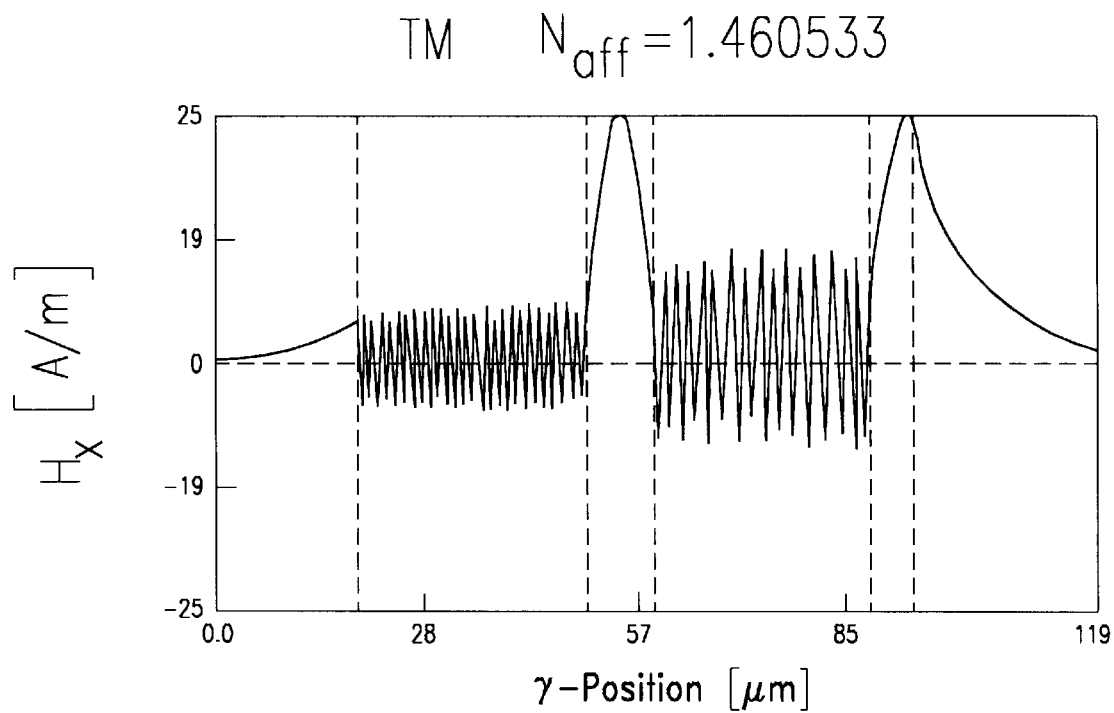
FIG. 11 shows field configurations for two modes having sharp central peaks and sharp side peaks useful for interferometric chemical sensors.
Figure 11B:
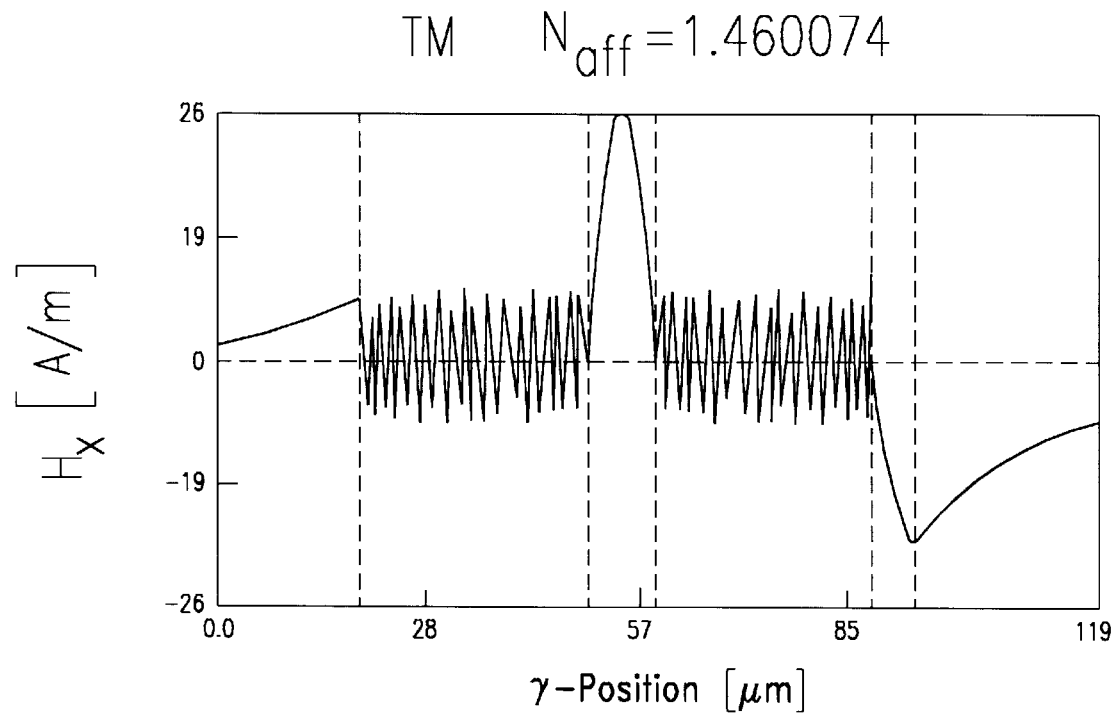

An additional advantage is a possibility to design chemical sensors of interferomertic type. We have found that the profile of multimode waveguide can be adjusted in such a way to exhibit two higher order modes having sharp central and side peaks. FIG. 11 shows an example of these modes in the case when $n_{cl}=1.46$, $n_1=1.463$, $n_2=1.65$, $n_3=1.463$, $d_1=8$ $\mu$m, $d_2=30$ $\mu$m, $d_3=5$ $\mu$m and $\lambda=1.55$ $\mu$m. An interferometric sensor described above but employing these two modes with sharp side peaks will detect a refractive index variation in outer low index layer and waveguide cladding being made from appropriate chemically sensitive material as a function of concentration of the substance to be detected. Note that all chemical sensors described are supposed to have a special chemically sensitive cladding reversibly reacting with the substance to be detected. In one preferred embodiment the sensor can posses a chemically sensitive outer layer at the interface between the waveguide core and cladding and also porous cladding providing for penetration of the substance.

The higher order modes with sharp central and side peaks can also find useful applications in electro-optical or all-optical modulators and other components described above if the cladding layer supporting sharp side peak is made from a material exhibiting electro-optical properties or third-order nonlinearity. It is usually more convenient to add such a material to the interface between waveguide core and cladding than to employ the core made from electro-optical or nonlinear material. Nonlinear optical polymers or poled polymers exhibiting electro-optical properties is one example of the practically useful material for such a cladding layer. Another option is to use electro-optical properties of fused silica interface between the core and cladding poled in strong electric field after its preheating. The electro-optical properties at the surface of poled fused silica have been recently demonstrated. The electro-optical properties of the outer layer can also be used to adjust the chemical sensors described above to the set point corresponding to a desired spectral region.

Applying the physical principles of this invention to different types of waveguides results in different types of waveguide sensors. For example, one can realize in such a way optical fiber sensors or integrated optical sensors based on both planar or rib waveguides.

For selective excitation and detection of the higher order modes with sharp peaks operating in all the components and sensors described one can also employ computer generated holograms. The same holograms can be used to select two modes whose interference is to be detected.

Another option for selection of a central peak of the operative mode is to butt-join a multimode waveguide with a single-mode output optical fiber. If the width of the central mode peak is matched to the width of the fundamental mode of this fiber, then it operates as an aperture providing good compatibility of the system with standard single-mode output network.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A multimode wavelength selective optical waveguide comprising:

a compound core with refractive index profile;

a cladding of lower refractive index;

said compound core having dimensions and in combination with a refractive index difference from said refractive index of said cladding, where said core and said cladding meet, such that an optical waveguide comprised of said core and cladding is a multimode optical waveguide able to propagate a large number of modes;

wherein said compound core has a dip within a central region of its refractive index profile providing propagation of a higher order mode in said waveguide having a sharp peak of said higher mode's field in said central region that carries a majority of the energy of said higher mode; and whereby said multimode optical waveguide by mode selection is wavelength selective and by said waveguide's output essentially functions as a single mode optical waveguide.

2. A multimode optical waveguide of claim 1, wherein said compound core has a step-index profile with said central dip.

3. A multimode optical waveguide of claim 1, wherein said compound core has a graded-index profile with said central dip.

4. A wavelength selective optical component for signal processing comprising a multimode optical waveguide of claim 1 optically connected with an input waveguide or a source of radiation and also with an output aperture or a waveguide that collects the energy curried by said central peak of said higher order mode and transmits it to a detector, wherein said refractive index profile of said compound waveguide core is adjusted in such a way to provide selection of the wavelength $\lambda$ in desired range of operation.

5. An amplitude sensor for detection of temperature variations, mechanical tensions, pressure, acoustic fields and other physical fields that are able to vary either refractive index or geometry of the sensing multimode optical waveguide of claim 1, wherein said refractive index profile of said multimode waveguide and/or the wavelength of operation are adjusted in such a way that the waveguide guides said higher order mode with sharp central peak near its cutoff to result in strong variation of the detected intensity of said central peak under the influence of external fields to be detected.

6. An interferometric sensor for detection of temperature variations, mechanical tensions, pressure, acoustic fields and other physical fields that are able to vary either refractive index or geometry of the sensing multimode optical waveguide of claim 1, wherein refractive index profile of said multimode waveguide and/or the wavelength of operation are adjusted in such a way that the waveguide guides two higher order modes with sharp central peaks of their fields carrying considerable part of their energies and the result of interference between two said peaks corresponding to said two modes is detected as a function of the external field to be detected.

7. A multimode optical waveguide according to claim 1, wherein said cladding has an additional layer at an interface between said core and said cladding, at least from one side of said waveguide, said layer having such thickness and refractive index as to provide conditions for propagation of a higher order mode in said waveguide having an additional sharp side peak of its field in said cladding at said interface between said core and said cladding and wherein said sharp side peak also carries a considerable part of the whole energy of said mode.

8. A chemical sensor based on a multimode optical waveguide of claim 7, wherein said waveguide is optically connected with an input waveguide or a source of radiation and also with an output aperture or a waveguide collecting the energy carried by said central peak of said higher order mode and transmitting it to a detector, said cladding and said layer at the interface between said core and said cladding comprise of chemically sensitive optical material whose refractive index, thickness or absorption depend on concentration of a substance in an external medium to be detected and result of the influence of said substance is detected as a variation in the intensity of said central peak of the mode in said waveguide.

9. A wavelength selective chemical sensor of claim 8, wherein said refractive index profile of said compound waveguide core is adjusted to the region near cutoff of said mode in such a way to provide selection of the wavelength $\lambda$ in desired spectral range corresponding to the line of strong absorption of said substance to be detected and to maximize sensitivity of the sensor.

10. A wavelength selective chemical sensor of claim 9, wherein said core or/and cladding of the waveguide are at least partially made from an electro-optic material to provide a possibility of adjusting the profile of the waveguide, said sensor has electrodes providing a possibility of applying an electric voltage to said electro-optic material for adjustment of its refractive index and said cladding is made from a porous chemically sensitive optical material such as polymers, glasses or ceramics, which is able to reversibly react with the substance to be detected.

11. A wavelength selective chemical sensor of claim 10 made from fused silica, wherein the surface of said compound core is poled in high electric field after its preheating in order to provide electro-optical properties in the interface layer between said core and said cladding.

12. A chemical sensor of interferometric type based of waveguide of claim 7, wherein said waveguide has such core refractive index profile that provides propagation of two said higher order modes with sharp central and side peaks of their fields, said additional layer and said lower index cladding supporting said side peaks of the mode fields are made of chemically sensitive material whose refractive index depends on concentration of the substance to be detected and the concentration of said substance is detected as a variation of the field intensity in the center of waveguide resulting from interference of the fields of said two higher order modes.

13. An elecrto-optical or acousto-optical modulator or switching components based on waveguide of claim 1, wherein said waveguides are at least partially made from materials exhibiting electro-opical or acousto-optical properties and have means to vary the refractive index profile of said waveguide using said properties in order to modulate an optical signal coming from said central peak of said higher order mode.

14. An elecrto-optical or acousto-optical modulator or switching components based on waveguide of claim 7, wherein said waveguides are at least partially made from materials exhibiting electro-opical or acousto-optical properties and have means to vary the refractive index profile of said waveguide using said properties in order to modulate an optical signal coming from said central peak of said higher order mode.

15. An all-optical modulator or switching component based on waveguide of claim 1, wherein said waveguide are at least partially made from third-order-nonlinear materials exhibiting dependence of their refractive index on the intensity of light irradiating said waveguide, said all-optical modulator has means to vary the intensity of said irradiating light in order to modulate the intensity of the output optical signal coming from said central peak of said higher order waveguide mode.

16. An all-optical modulator or switching component based on waveguide of claim 7, wherein said waveguide are at least partially made from third-order-nonlinear materials exhibiting dependence of their refractive index on the intensity of light irradiating said waveguide, said all-optical modulator has means to vary the intensity of said irradiating light in order to modulate the intensity of the output optical signal coming from said central peak of said higher order waveguide mode.

17. An optical bistable component for logic switching and optical memory applications comprising the all-optical waveguide modulator of claim 15 and means for optical feedback, said means can comprise either a mirrors or an optical fiber loop.

18. An optical bistable component for logic switching and optical memory applications comprising the all-optical waveguide modulator of claim 16 and means for optical feedback, said means can comprise either a mirrors or an optical fiber loop.

19. Optical waveguide components and sensors based on waveguide of claim 1, wherein at least some part of said compound core of said multimode waveguide is made of a material exhibiting electro-optical properties and said component has means to apply an electric voltage to vary refractive index of said core material in order to adjust refractive index profile of the core to desired range of operation wavelengths and desired sensitivity.

20. Optical waveguide components and sensors based on waveguide of claim 7, wherein at least some part of said compound core of said multimode waveguide is made of a material exhibiting electro-optical properties and said component has means to apply an electric voltage to vary refractive index of said core material in order to adjust refractive index profile of the core to desired range of operation wavelengths and desired sensitivity.

21. Optical waveguide components and sensors based on waveguide of claim 1, wherein said multimode waveguide is an optical fiber.

22. Optical waveguide components and sensors based on waveguide of claim 7, wherein said multimode waveguide is an optical fiber.

23. Optical waveguide components and sensors based on waveguide of claim 1, wherein multimode waveguide is a planar or rib integrated optical waveguide.

24. Optical waveguide components and sensors based on waveguide of claim 7, wherein multimode waveguide is a planar or rib integrated optical waveguide.

25. All-fiber in line optical waveguide components and sensors of claim 21, wherein said multimode optical waveguide, said input waveguide and said output waveguide are optical fibers.

26. All-fiber in line optical waveguide components and sensors of claim 22, wherein said multimode optical waveguide, said input waveguide and said output waveguide are optical fibers.

27. Optical waveguide components and sensord based on waveguide of claim 1, wherein a single-mode fiber optically connected to said multimode waveguide is used as said aperture for selection of said energy of said central mode peak.

28. Optical waveguide components and sensors based on waveguide of claim 7, wherein a single-mode fiber optically connected to said multimode waveguide is used as said aperture for selection of said energy of said central mode peak.

29. Optical waveguide components and sensors based on waveguide of claim 1, wherein said profile of multimode waveguide is adjusted in such a way to get desired width of the output central peak of said mode.

30. Optical waveguide components and sensors based on waveguide of claim 7, wherein said profile of multimode waveguide is adjusted in such a way to get desired width of the output central peak of said mode.

31. Optical waveguide components or sensors based on waveguide of claim 1, wherein width of said central peak of the higher order mode field in said multimode waveguide is matched to the width of the fundamental mode of the output single-mode fiber network.

32. Optical waveguide components or sensors based on waveguide of claim 7, wherein width of said central peak of the higher order mode field in said multimode waveguide is matched to the width of the fundamental mode of the output single-mode fiber network.

33. Optical waveguide components or sensors based on waveguide of claim 1, wherein a computer generated hologram is employed to select either one operating made having sharp peaks or two such modes whose interference to be detected.

34. Optical waveguide components or sensors based on waveguide of claim 7, wherein a computer generated hologram is employed to select either one operating mode having sharp peaks or two such modes whose interference to be detected.

35. Optical waveguide components or sensors based on waveguide of claim 1, wherein a computer generated holograms are employed to selectively excite and detect either one operating mode having sharp peaks or two such modes whose interference to be detected.

36. Optical waveguide components or sensors based on waveguide of claim 7, wherein a computer generated holograms are employed to selectively excite and detect either one operating mode having sharp peaks or two such modes whose interference to be detected.

* * * * *